(12) United States Patent
Abe

(10) Patent No.: US 11,344,238 B2
(45) Date of Patent: May 31, 2022

(54) ATTACHMENT TAPE AND PULSE PHOTOMETRY PROBE

(71) Applicant: NIHON KOHDEN CORPORATION, Tokyo (JP)

(72) Inventor: Takahiro Abe, Tokorozawa (JP)

(73) Assignee: NIHON KOHDEN CORPORATION, Tokyo (JP)

(*) Notice: Subject to any disclaimer, the term of this patent is extended or adjusted under 35 U.S.C. 154(b) by 543 days.

(21) Appl. No.: 15/849,788

(22) Filed: Dec. 21, 2017

(65) Prior Publication Data

US 2018/0177424 A1    Jun. 28, 2018

(30) Foreign Application Priority Data

Dec. 27, 2016  (JP) ............................. JP2016-253654

(51) Int. Cl.
  *A61B 5/1455*  (2006.01)
  *A61B 5/259*   (2021.01)
  (Continued)

(52) U.S. Cl.
  CPC ............ *A61B 5/259* (2021.01); *A61B 5/0059* (2013.01); *A61B 5/02416* (2013.01);
  (Continued)

(58) Field of Classification Search
  CPC . A61B 5/688; A61B 5/04087; A61B 5/02416; A61B 5/0059; A61B 5/1455; A61B 5/14551; A61B 5/14552; A61B 5/6826; A61B 5/6832; A61B 5/6829; A61B 5/259; A61B 5/6838; A61B 5/411; A61B 5/0205
  See application file for complete search history.

(56) References Cited

U.S. PATENT DOCUMENTS 4,830,014 A * 5/1989 Goodman .......... A61B 5/02427
                                                600/310
4,981,133 A * 1/1991 Rollband ............. A61B 17/132
                                                128/888
(Continued)

FOREIGN PATENT DOCUMENTS

CN         2584162 Y    11/2003
CN       201510423 U     6/2010
(Continued)

OTHER PUBLICATIONS

Japanese Office Action issued in Japanese Patent Application No. 2016-253654 dated Sep. 23, 2020.
(Continued)

*Primary Examiner* — Chu Chuan Liu
(74) *Attorney, Agent, or Firm* — Pearne & Gordon LLP

(57) ABSTRACT

An attachment tape is configured such that a light emitter and a light detector are mounted on the attachment tape and such that the attachment tape is wrapped around a tissue so as to be attached to the tissue. The light emitter is configured to emit light. The light detector is configured to detect the light emitted from the light emitter. A width dimension of the attachment tape is gradually narrowed from one point along a longitudinal direction of the attachment tape toward another point at a distal end of the attachment tape.

19 Claims, 5 Drawing Sheets

(51) Int. Cl.
*A61B 5/00* (2006.01)
*A61B 5/024* (2006.01)

(52) U.S. Cl.
CPC ........ *A61B 5/14552* (2013.01); *A61B 5/6826* (2013.01); *A61B 5/6829* (2013.01); *A61B 5/6832* (2013.01); *A61B 5/411* (2013.01); *A61B 5/6838* (2013.01)

(56) References Cited

U.S. PATENT DOCUMENTS

| | | | | |
|---|---|---|---|---|
| 5,830,136 | A * | 11/1998 | Delonzor | A61B 5/14552 600/323 |
| 5,913,819 | A * | 6/1999 | Taylor | A61B 5/6833 600/323 |
| 6,061,584 | A * | 5/2000 | Lovejoy | A61B 5/14552 600/344 |
| 6,119,027 | A * | 9/2000 | Selenberger | A61B 5/14552 600/310 |
| 6,545,193 | B1 * | 4/2003 | Morgenstern | A61F 13/0273 128/876 |
| 6,671,532 | B1 * | 12/2003 | Fudge | A61B 5/14552 221/26 |
| 6,920,345 | B2 * | 7/2005 | Al-Ali | A61B 5/6833 600/344 |
| 8,726,496 | B2 * | 5/2014 | Besko | A61B 5/7203 29/831 |
| 8,825,126 | B2 * | 9/2014 | Murozono | A61B 5/6831 600/323 |
| 9,161,722 | B2 * | 10/2015 | Besko | A61B 5/68335 |
| 9,592,000 | B2 * | 3/2017 | Shimuta | A61B 5/688 |
| 10,463,340 | B2 * | 11/2019 | Telfort | A61B 7/003 |
| 2002/0045807 | A1 | 4/2002 | Al-Ali et al. | |
| 2003/0004450 | A1 | 1/2003 | Falleiros et al. | |
| 2003/0055369 | A1 | 3/2003 | Siegwart et al. | |
| 2003/0093024 | A1 | 5/2003 | Falleiros et al. | |
| 2003/0100840 | A1 * | 5/2003 | Sugiura | A61B 5/6838 600/504 |
| 2003/0135146 | A1 * | 7/2003 | Daneshvar | A61F 13/066 602/60 |
| 2004/0147821 | A1 | 7/2004 | Al-Ali et al. | |
| 2007/0123756 | A1 * | 5/2007 | Kitajima | A61B 5/14552 600/300 |
| 2008/0076987 | A1 * | 3/2008 | Arizaga Ballesteros | A61B 5/14552 600/323 |
| 2008/0076995 | A1 * | 3/2008 | Hoarau | A61B 5/14552 600/344 |
| 2010/0312160 | A1 * | 12/2010 | Creighton | A61L 15/42 602/62 |
| 2010/0318195 | A1 | 12/2010 | Kettwig et al. | |
| 2012/0220842 | A1 * | 8/2012 | Parker | A61B 5/6826 600/323 |
| 2013/0171599 | A1 * | 7/2013 | Bleich | A61B 5/486 434/247 |
| 2014/0128790 | A1 * | 5/2014 | Nokes, Jr. | A61F 13/0259 602/54 |
| 2016/0022442 | A1 | 1/2016 | Kettwig et al. | |
| 2016/0120465 | A1 * | 5/2016 | Parfenova | A61B 5/4818 600/301 |
| 2017/0020400 | A1 * | 1/2017 | Rinderknecht | A61B 5/02438 |
| 2017/0157915 | A1 * | 6/2017 | Roth | B44D 2/002 |
| 2017/0311891 | A1 * | 11/2017 | Kiani | A61B 5/6833 |
| 2018/0098707 | A1 * | 4/2018 | Salamon | A61B 5/02416 |
| 2019/0239758 | A1 * | 8/2019 | Park | A61B 5/02108 |
| 2019/0274574 | A1 * | 9/2019 | Hughes | A61B 7/04 |
| 2019/0343432 | A1 * | 11/2019 | Harris | A61B 5/6826 |

FOREIGN PATENT DOCUMENTS

| | | |
|---|---|---|
| CN | 101842049 A | 9/2010 |
| CN | 202526668 U | 11/2012 |
| CN | 203354765 U | 12/2013 |
| CN | 105232057 A | 1/2016 |
| EP | 0 127 947 B1 | 12/1984 |
| JP | H04-131238 U | 12/1992 |
| JP | H06-105917 A | 4/1994 |
| JP | 2003-052741 A | 2/2003 |
| JP | 2003-135513 A | 5/2003 |
| JP | 2003-225215 A | 8/2003 |
| JP | 2007-105316 A | 4/2007 |

OTHER PUBLICATIONS

Chinese Office Action dated Dec. 7, 2021 issued in Chinese Patent Application No. 201711443718.8.

* cited by examiner

ATTACHMENT TAPE AND PULSE PHOTOMETRY PROBE

CROSS-REFERENCE TO RELATED APPLICATION

The present application claims priority from Japanese Patent Application No. 2016-253654 filed on Dec. 27, 2016, the entire content of which is incorporated herein by reference.

BACKGROUND

The presently disclosed subject matter relates to an attachment tape and a pulse photometry probe.

Related art pulse photometry probes include a pulse oximetry probe configured to be wrapped around a tissue of a patient (e.g., a finger, a hand or a foot) to measure physiological information (e.g., arterial oxygen saturation (SpO2) on blood vessels inside the tissue. For example, U.S. Pat. No. 5,830,136A discloses a sensor having a cover layer, a light emitter and a light detector disposed on one side of the cover layer, a gel support layer provided on the same side of the cover layer, and a gel layer provided on the gel support layer to contact a tissue such as a finger of a patient. The shape of the sensor is rectangular in a plan view. In other words, the dimension of the sensor in the width direction (the width dimension) perpendicular to the longitudinal direction thereof is constant.

Since the width dimension of the sensor is constant along the longitudinal direction of the sensor, lateral faces of the sensor (more specifically, lateral faces of the cover layer, the gel support layer and the gel layer) are aligned with respect to the width direction when the sensor is wrapped around a finger of a patient. Thus, in a case where an object, such as a hand or a foot of the patient, hits the lateral face of the sensor, a contact area between the lateral face of the sensor and the hitting object is large, so that the sensor may move largely with respect to the finger. In the worst case, the sensor may come off the finger.

SUMMARY

The presently disclosed subject matter provides an attachment tape capable of being wrapped securely around a tissue such as a finger of a patient, and also provides a pulse photometry probe having the attachment tape.

According to an aspect of the presently disclosed subject matter, an attachment tape is configured such that a light emitter and a light detector are mounted on the attachment tape and such that the attachment tape is wrapped around a tissue so as to be attached to the tissue. The light emitter is configured to emit light. The light detector is configured to detect the light emitted from the light emitter. A width dimension of the attachment tape is gradually narrowed from one point along a longitudinal direction of the attachment tape toward another point at a distal end of the attachment tape.

DETAILED DESCRIPTION

Figure 1:
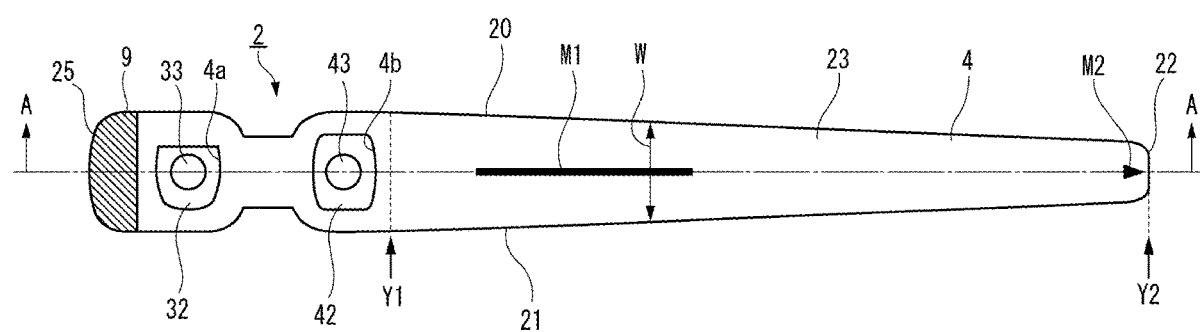
FIG. 1 is a plan view of an attachment tape according to an embodiment of the presently disclosed subject matter, viewed from a +Z position.
Figure 1:
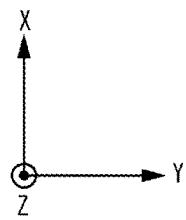

Hereinafter, embodiments of the presently disclosed subject matter will be described with reference to the drawings. The dimensions of each parts shown in the drawings may not be to scale for illustrative purpose.

In the following description, a reference will be made to an X-axis direction, a Y-axis direction and a Z-axis direction for illustrative purpose. These directions are defined in relation to the attachment tape 2 shown in FIG. 1. The X-axis direction includes a +X direction (the direction of the arrow in the drawings) and a −X direction (the direction opposite the direction of the arrow). The Y-axis direction includes a +Y direction (the direction of the arrow in the drawings) and a −Y direction (the direction opposite the direction of the arrow). The Z-axis direction includes a +Z direction (the direction of the arrow in the drawing) and a −Z direction (the direction opposite the direction of the arrow).

Figure 2:
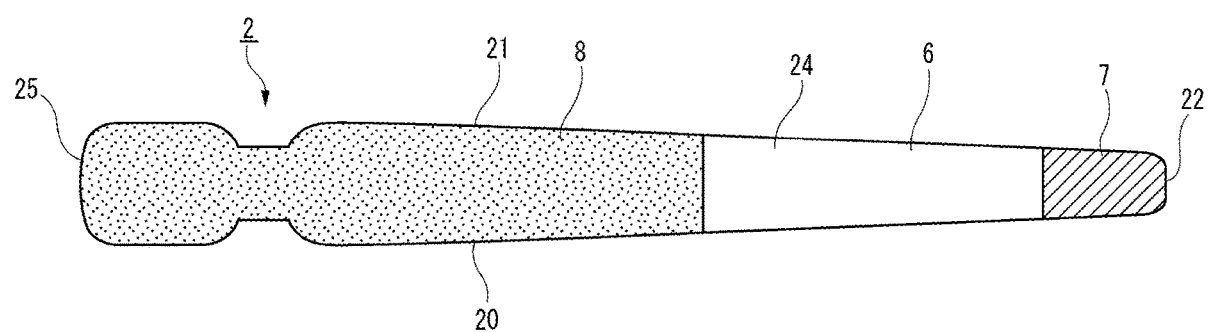
FIG. 2 is a plan view of the attachment tape, viewed from a −Z position.
Figure 2:
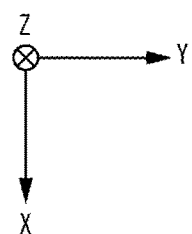
Figure 3:
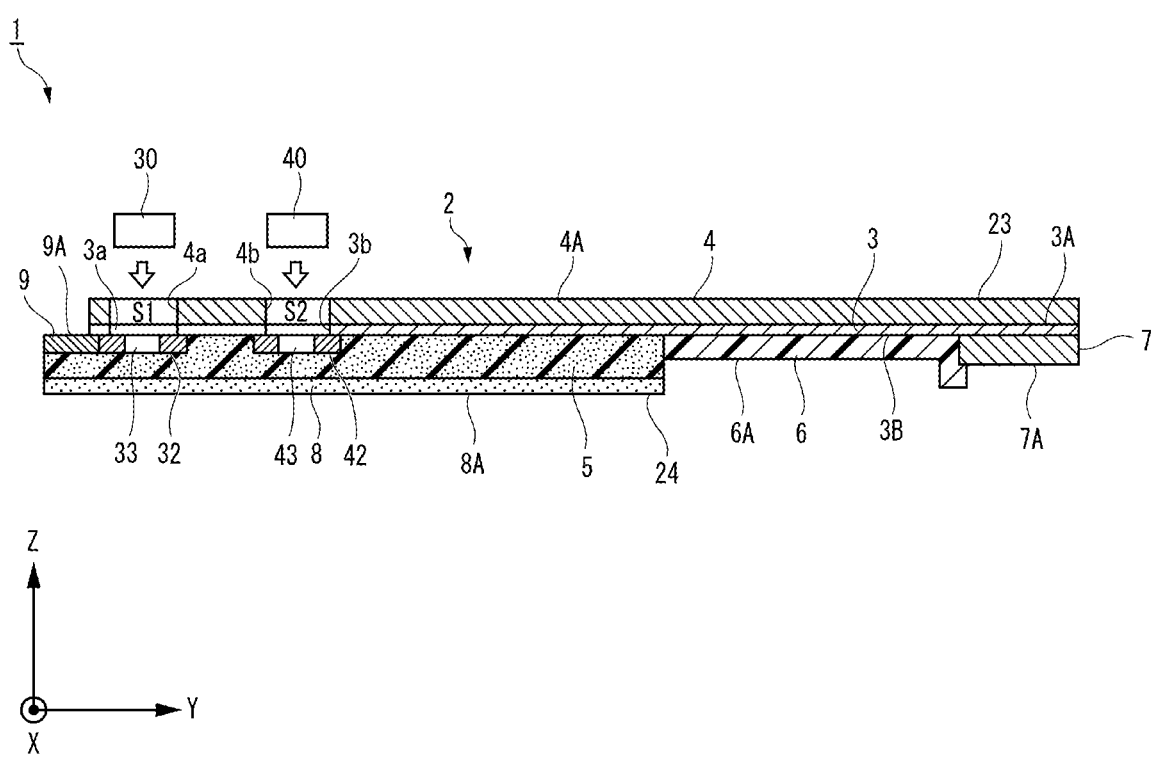
FIG. 3 is a cross sectional view of the attachment tape shown in FIG. 1, taken along the line A-A of FIG. 1.
Figure 4:
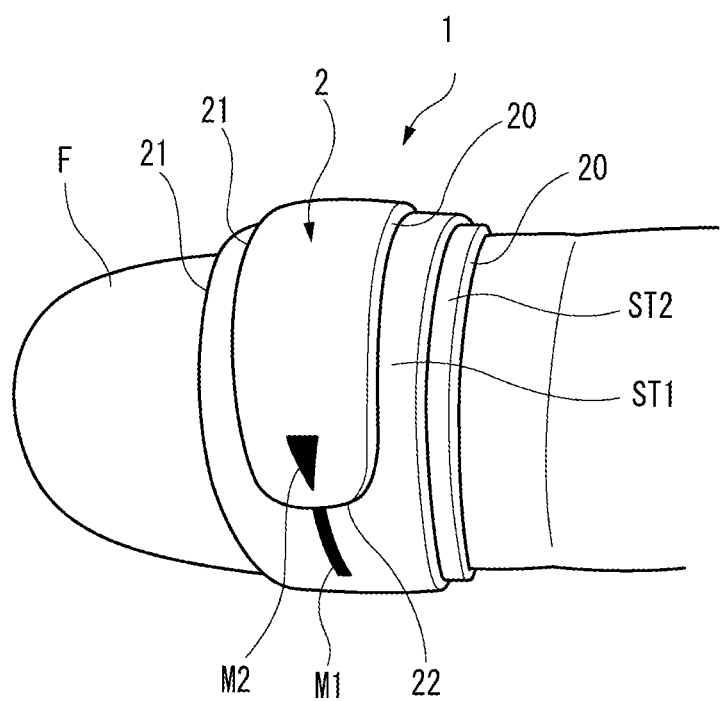
FIG. 4 illustrates the attachment tape wrapped around a finger of a patient.

FIG. 1 is a plan view of the attachment tape 2 according to the embodiment of the presently disclosed subject matter, viewed from a +Z position. FIG. 2 is a plan view of the attachment tape 2, viewed from a −Z position. FIG. 3 is a cross sectional view of the attachment tape 2 shown in FIG. 1, taken along the line A-A of FIG. 1. FIG. 4 illustrates the attachment tape 2 wrapped around a finger F of a patient (an example of a tissue). As shown in FIG. 3, the attachment tape 2 is configured such that a light emitter 30 and a light detector 40 are mounted on the attachment tape 2. The light emitter 30 is configured to emit light, and a light detector 40 is configured to detect the light emitted from the light emitter 30. The arrangement of the light emitter 30 and the light detector 40 may be exchanged. The light emitter 30 and the light detector 40 are mounted on the attachment tape 2 to form a pulse photometry probe 1 (hereafter, simply referred to as the probe 1) is configured. In other words, the probe 1 includes the light emitter 30, the light detector 40 and the attachment tape 2. The probe 1 is, for example, a pulse oximetry probe of a disposable type that can measure arterial oxygen saturation (SpO2) by wrapping the probe around a tissue such as a finger of a patient. As shown in FIG. 4, the attachment tape 2 is configured to be attached to a finger F of a patient by being wrapped around the finger F.

The light emitter 30 may include a sub-mount substrate, two light emitting devices and a lens covering the two light emitting devices. The two light emitting devices may be mounted on the sub-mount substrate while being arranged in parallel in the X-axis direction. The light emitting device is, for example, a light-emitting diode (LED). For example, in the case that the probe 1 is a pulse oximetry probe, one of the two light emitting devices is a red light LED that emits red light, and the other of the two light emitting devices is an infrared light LED that emits infrared light. The number of the light emitting devices is not particularly limited, and the number may be one or three or more. Furthermore, the emission wavelengths of the light emitting devices are not particularly limited either.

The light detector 40 is configured to detect the light emitted from the light emitting devices of the light emitter 30 and transmitted through or reflected by the finger F. The light detector 40 includes one or more light-detecting devices, such as photodiodes (PDs). The number of the light-detecting devices is not particularly limited. For example, in the case that the probe 1 is a pulse oximetry probe, one light-detecting device may detect the red light emitted from the red light LED and the infrared light emitted from the infrared light LED.

The oxyhemoglobin contained in the blood flowing through the blood vessels of the finger F has a large light absorption amount for the infrared light. On the other hand, the deoxyhemoglobin contained in the blood has a large light absorption amount for the red light. Hence, SpO2 can be measured by detecting the changes in the amounts of the infrared light and the red light emitted from the light emitter 30 and transmitted through the finger F (more particularly, the blood vessels of the finger F) using the light detector 40.

The attachment tape 2 includes a double-sided tape layer 3, a hook-and-loop fastener layer 4, a sponge layer 5, an outer tape layer 6, a hook-and-loop fastener layer 7, an adhesive layer 8, an anti-slip layer 9, and double-sided tape layers 32 and 42. The double-sided tape layer 3 is coated with an adhesive and has faces 3A and 3B positioned opposed to each other and through holes 3a and 3b extending from the face 3A to the face 3B of the double-sided tape layer 3. The hook-and-loop fastener layer 4 is composed of a plurality of loop members and disposed on the face 3A of the double-sided tape layer 3. The hook-and-loop fastener layer 4 has a through hole 4a communicating with the through hole 3a and a through hole 4b communicating with the through hole 3b. The area of the through hole 3a may coincide with the area of the through hole 4a, and the area of the through hole 3b may coincide with the area of the through hole 4b in a plan view. The accommodation space S1 for accommodating the light emitter 30 is defined by the through hole 3a and the through hole 4a. Furthermore, the accommodation space S2 for accommodating the light detector 40 is defined by the through hole 3b and the through hole 4b. The face 4A of the hook-and-loop fastener layer 4 forms a portion of the first face 23 of the attachment tape 2 (see, e.g., FIG. 1).

The sponge layer 5 is disposed on the face 3B of the double-sided tape layer 3. The sponge layer 5 is made of a soft material having air permeability. For example, the sponge layer 5 may be made of urethane, polyethylene, silicon, melamine, acrylic, ethylene-vinyl acetate (EVA) copolymer resin, rubber sponge, polyolefin, elastomer, polyamide, polyester, poly-nylon, polystyrene, etc. Furthermore, the outer tape layer 6 and the hook-and-loop fastener layer 7 are disposed on the face 3B of the double-sided tape layer 3. The hook-and-loop fastener layer 7 is composed of a plurality of hook members. In a state in which the attachment tape 2 is wrapped around the finger F, each of the plurality of hook members of the hook-and-loop fastener layer 7 is engaged with one of the plurality of loop members of the hook-and-loop fastener layer 4, whereby the hook-and-loop fastener layer 7 is fixed to the hook-and-loop fastener layer 4.

The adhesive layer 8 is disposed on the sponge layer 5. In a state in which the attachment tape 2 is wrapped around the finger F, the face 8A of the adhesive layer 8 directly contacts the finger F. The attachment tape 2 can be wrapped around the finger F securely by the adhesive layer 8 (in other words, it is possible to appropriately prevent a situation in which the attachment tape 2 comes off the finger F). The dimension of the adhesive layer 8 in the Y-axis direction (the length dimension) and the length dimension of the sponge layer 5 are set to the extent that the adhesive layer 8 can cover the outer circumference of the finger F in a state in which the attachment tape 2 is wrapped around the finger F. Since the attachment tape 2 is provided with the sponge layer 5, the air permeability of the attachment tape 2 can be secured, and the load (tightening force) applied to the finger F around which the attachment tape 2 is wrapped can be relieved. Each of the face 8A of the adhesive layer 8, the face 6A of the outer tape layer 6 and the face 7A of the hook-and-loop fastener layer 7 forms a portion of the second face 24 of the attachment tape 2 (see, e.g., FIG. 2). The second face 24 of the attachment tape 2 opposite the first face 23 of the attachment tape 2, and the face 8A of the adhesive layer 8 forming a portion of the second face 24 is arranged to contact the finger F.

The anti-slip layer 9 is provided on the sponge layer 5 and has a smooth face 9A that contacts the adhesive layer 8 in a state in which the attachment tape 2 is wrapped around the finger F. The smooth face 9A forms a portion of the first face 23 of the attachment tape 2. The static friction coefficient between the smooth face 9A of the anti-slip layer 9 and the face 8A of the adhesive layer 8 is larger than the static friction coefficient between the face 4A of the hook-and-loop fastener layer 4 and the face 8A of the adhesive layer 8. Hence, the anti-slip layer 9 can properly suppress the slip between the face 8A of the adhesive layer 8 (a portion of the second face 24 of the attachment tape 2) and the hook-and-loop fastener layer 4 (a portion of the first face 23 of the attachment tape 2).

The double-sided tape layer 32 is provided in the first concave section (not shown) of the sponge layer 5. The light emitter 30 is bonded to the double-sided tape layer 32 while being disposed in the accommodation space S1. The double-sided tape layer 32 has an opening 33 through which the light emitted from the light emitter 30 passes. The double-sided tape layer 42 is provided in the second concave section (not shown) of the sponge layer 5. The light detector 40 is bonded to the double-sided tape layer 42 while being disposed in the accommodation space S2. The double-sided tape layer 42 has an opening 43 through which the light incident on the light detector 40 passes.

Next, the outer shape of the attachment tape 2 in a plan view will be described referring to FIG. 1. As shown in FIG. 1, the dimension of the attachment tape 2 in the X-axis direction (the width dimension W) is gradually narrowed from one point Y1 along the longitudinal direction (the Y-axis direction) toward another point Y2 at the distal end 22 of the attachment tape 2 (the distal end position). The position Y1 may herein be in the vicinity of the through hole 4b in which the light detector 40 is accommodated or may be any position between the base end 25 and the distal end 22 of the attachment tape 2 in the Y-axis direction. For instance, the width dimension W of the attachment tape 2 may be gradually narrowed from the base end 25 to the distal end 22.

With this embodiment, the width dimension W of the attachment tape 2 is gradually narrowed from the point Y1 along the Y-axis direction toward the distal end position Y2. Hence, in a state in which the attachment tape 2 is wrapped around the finger F, the first lateral face 20 of the attachment tape 2 is not aligned in the X-axis direction of the attachment tape 2 (see FIG. 4). Same or similarly, the second lateral face 21 of the attachment tape 2 is not aligned with respect to the X-axis direction of the attachment tape 2. In other words, as shown in FIG. 4, in a state in which the attachment tape 2 is wrapped around the finger F, step portions St1 and St2 are formed on the attachment tape 2. For example, even when the first lateral face 20 of the attachment tape 2 is hit by an object, such as a hand or a foot of the patient, the area of the first lateral face 20 of the attachment tape 2 that contacts the object is small, so that the attachment tape 2 wrapped around the finger F is prevented from coming off the finger F. In this manner, the attachment tape 2 capable of being wrapped securely around the finger F is provided.

As shown in FIGS. 1 to 4, guide marks M1 and M2 are provided on the first face 23 of the attachment tape 2 (the face 4A of the hook-and-loop fastener layer 4). The guide marks M1 and M2 are configured to guide the distal end 22 of the attachment tape 2 to a position at or adjacent to the center of the attachment tape 2 with respect to the X-axis direction (the width direction) perpendicular to the Y-axis direction of the attachment tape 2. The shape of the guide mark M1 may be triangular. Moreover, the position of the guide mark M2 with respect to the Y-axis direction is adjacent to the distal end position Y2, and the position of the guide mark M2 with respect to the X-axis direction is at or adjacent to the center of the attachment tape 2 with respect to the X-axis direction. The shape of the guide mark M1 may be a line segment having a predetermined length and a predetermined width. The position of the guide mark M1 with respect to the Y-axis direction is at or adjacent to a position where the distal end 22 is expected to be attached in place in a state in which the attachment tape 2 is wrapped around the finger F, and the position of the guide mark M1 with respect to the X-axis direction is at or adjacent to the center of the attachment tape 2 with respect to the X-axis direction. The forms of the guide marks M1 and M2 are not particularly limited. For example, the guide mark M1 may represent a certain shape. While the two guide marks M1 and M2 are provided in this embodiment, only the guide mark M1 may be provided on the first face 23 of the attachment tape 2. Even in this case, the distal end 22 of the attachment tape 2 can be guided to the center of the attachment tape 2 in the X-axis direction.

With this embodiment, the patient or a medical worker is urged by the guide marks M1 and M2 to wrap the attachment tape 2 around the finger F of the patient such that the distal end 22 of the attachment tape 2 is positioned at or adjacent to the center of the attachment tape 2 with respect to the X-axis direction. As a result, it is possible to avoid a situation in which the distal end 22 is in a state of protruding to the outside from the first lateral face 20 or the second lateral face 21 of the attachment tape 2 and injuring the patient's body.

Figure 5:
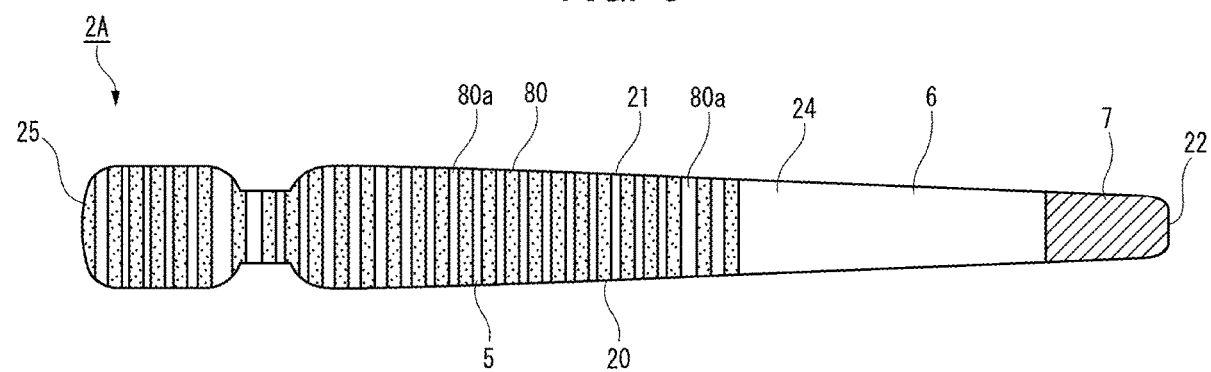
FIG. 5 is a plan view of an attachment tape according to another embodiment of the presently disclosed subject matter, viewed from the −Z position.
Figure 5:
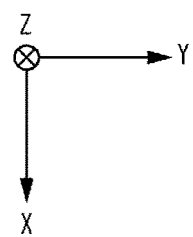

Next, an attachment tape 2A according to another embodiment will be described referring to FIG. 5. FIG. 5 is a plan view of the attachment tape 2A, viewed from the −Z position. As shown in FIG. 5, the attachment tape 2A is different from the attachment tape 2 in that the attachment tape 2A is provided with an adhesive layer 80 instead of the adhesive layer 8. The adhesive layer 80 has a plurality of opened portions 80a (exposing portions) arranged in parallel in the Y-axis direction, and the sponge layer 5 is exposed through the plurality of opened portions 80a. Since the adhesive layer 80 has the plurality of opened portions 80a as described above, the air permeability of the attachment tape 2 can be secured, and the attachment tape 2A can be securely wrapped around the finger F by the adhesive layer 80. Consequently, it is possible to improve the air permeability and the attaching performance of the attachment tape 2A.

While the presently disclosed subject matter has been described with reference to certain exemplary embodiments thereof, the scope of the presently disclosed subject matter is not limited to the exemplary embodiments described above, and it will be understood by those skilled in the art that various changes and modifications may be made therein without departing from the scope of the presently disclosed subject matter as defined by the appended claims.

What is claimed is:

1. An attachment tape configured such that a light emitter and a light detector are mounted on the attachment tape and such that the attachment tape is capable of being wrapped around and attached to a tissue, the light emitter being configured to emit light and the light detector being configured to detect the light emitted from the light emitter, wherein the attachment tape includes:
   a first part where the light emitter is accommodated;
   a second part where the light detector is accommodated;
   a third part between the first part and second part; and
   a fourth part that extends from the second part to a distal end of the attachment tape,
   wherein the third part has a constant width that is smaller than a width of the first part and a width of the second part,
   wherein a width dimension of the forth part is gradually narrowed from one point along a longitudinal direction of the attachment tape toward another point at the distal end of the attachment tape, and
   wherein the light emitter and light detector are both located along a centerline of the attachment tape with respect to a width direction of the attachment tape, the width direction being perpendicular to the longitudinal direction.

2. The attachment tape according to claim 1, comprising:
   a first face; and
   a second face opposite the first face,
   wherein a guide mark is provided on the first face, the guide mark being configured to guide the distal end of the attachment tape to a position at or adjacent to the centerline of the attachment tape with respect to the width direction.

3. The attachment tape according to claim 1, comprising:
   an adhesive layer; and
   an anti-slip layer having a smooth face arranged to contact the adhesive layer in a state in which the attachment tape is wrapped around the tissue.

4. The attachment tape according to claim 2, comprising:
   an adhesive layer; and
   an anti-slip layer having a smooth face arranged to contact the adhesive layer in a state in which the attachment tape is wrapped around the tissue,
   wherein a face of the adhesive layer forms a portion of the second face of the attachment tape, and the smooth face of the anti-slip layer forms a portion of the first face of the attachment tape.

5. The attachment tape according to claim 3, further comprising a sponge layer, wherein the adhesive layer is formed on the sponge layer.

6. The attachment tape according to claim 5, wherein the adhesive layer has a plurality of exposing portions through which a face of the sponge layer is exposed.

7. The attachment tape according to claim 1, further comprising a guide mark on the attachment tape that is located along the centerline of the attachment tape with respect to the width direction.

8. The attachment tape according to claim 1, comprising:
   a first face; and
   a second face opposite the first face,
   wherein the first face includes a through hole that accommodates the light emitter and another through hole that accommodates the light detector.

9. A pulse photometry probe comprising:
a light emitter configured to emit light;
a light detector configured to detect the light emitted from the light emitter; and
an attachment tape having a first face and a second face opposite to the first face, the attachment tape including:
a first part where the light emitter is accommodated,
a second part where the light detector is accommodated,
a third part between the first part and second part; and
a fourth part that extends from the second part to a distal end of the attachment tape,
wherein the third part has a constant width that is smaller than a width of the first part and a width of the second part,
wherein the attachment tape is configured such that the light emitter and the light detector are mounted on the attachment tape and such that the attachment tape is capable of being wrapped around and attached to a tissue,
wherein a width dimension of the fourth part is gradually narrowed from one point along a longitudinal direction of the attachment tape toward another point at the distal end of the attachment tape, and
wherein the light emitter and light detector are both located along a centerline of the attachment tape with respect to a width direction of the attachment tape, the width direction being perpendicular to the longitudinal direction.

10. The pulse optometry probe according to claim 9, further comprising a guide mark on the attachment tape that is located along the centerline of the attachment tape with respect to the width direction.

11. The attachment tape according to claim 9, wherein the first face includes a through hole that accommodates the light emitter and another through hole that accommodates the light detector.

12. An attachment tape configured such that a light emitter and a light detector are mounted on the attachment tape and such that the attachment tape is capable of being wrapped around and attached to a tissue, the light emitter being configured to emit light and the light detector being configured to detect the light emitted from the light emitter, wherein the attachment tape includes:
a first part where the light emitter is accommodated;
a second part where the light detector is accommodated;
a third part between the first part and second part; and
a fourth part a fourth part that extends from the second part to a distal end of the attachment tape,
wherein the third part has a constant width that is smaller than a width of the first part and a width of the second part,
wherein the attachment tape is configured to be rolled about the tissue a plurality of turns, the plurality of turns including an inner turn and an outer turn, and
wherein a width dimension of the fourth part is gradually narrowed along a roll direction of the attachment tape such that a width of the inner turn is greater than a width of the outer turn.

13. The attachment tape according to claim 12, comprising:
a first face; and
a second face opposite the first face,
wherein a guide mark is provided on the first face, the guide mark being configured to guide the distal end of the attachment tape to a position at or adjacent to a centerline of the attachment tape with respect to a width direction of the attachment tape.

14. The attachment tape according to claim 12, comprising:
an adhesive layer; and
an anti-slip layer having a smooth face arranged to contact the adhesive layer in a state in which the attachment tape is wound around the tissue.

15. The attachment tape according to claim 13, comprising:
an adhesive layer; and
an anti-slip layer having a smooth face arranged to contact the adhesive layer in a state in which the attachment tape is wrapped around the tissue,
wherein a face of the adhesive layer forms a portion of the second face of the attachment tape, and the smooth face of the anti-slip layer forms a portion of the first face of the attachment tape.

16. The attachment tape according to claim 12, further comprising:
an adhesive layer; and
a sponge layer, wherein the adhesive layer is formed on the sponge layer.

17. The attachment tape according to claim 16, wherein the adhesive layer has a plurality of exposing portions through which a face of the sponge layer is exposed.

18. The attachment tape according to claim 12, further comprising a guide mark on the attachment tape that is located along a centerline of the attachment tape with respect to the width direction.

19. The attachment tape according to claim 12, comprising:
a first face; and
a second face opposite the first face,
wherein the first face includes a through hole that accommodates the light emitter and another through hole that accommodates the light detector.

* * * * *